United States Patent
Chilkoti et al.

(10) Patent No.: US 7,129,096 B2
(45) Date of Patent: Oct. 31, 2006

(54) SENSOR FOR USE IN TESTING BIOLOGICAL, BIOCHEMICAL, CHEMICAL OR ENVIRONMENTAL SAMPLES

(75) Inventors: Ashutosh Chilkoti, Durham, NC (US); Nidhi Nath, Durham, NC (US); Wolfgang Frey, Austin, TX (US)

(73) Assignee: Duke University, Durham, NC (US)

( * ) Notice: Subject to any disclaimer, the term of this patent is extended or adjusted under 35 U.S.C. 154(b) by 661 days.

(21) Appl. No.: 10/315,149

(22) Filed: Dec. 10, 2002

(65) Prior Publication Data

US 2003/0170687 A1 Sep. 11, 2003

Related U.S. Application Data

(60) Provisional application No. 60/338,688, filed on Dec. 11, 2001.

(51) Int. Cl.
*G01N 33/543* (2006.01)
(52) U.S. Cl. ............... 436/518; 422/82.05; 422/82.11; 435/5; 435/6; 435/7.2; 435/7.4; 436/524; 436/525; 436/164; 436/165; 436/805; 436/817; 436/827
(58) Field of Classification Search ............... None
See application file for complete search history.

(56) References Cited

U.S. PATENT DOCUMENTS

| | | | |
|---|---|---|---|
| 5,242,828 A | 9/1993 | Bergström et al. | ......... 435/291 |
| 5,436,161 A | 7/1995 | Bergström et al. | ......... 435/291 |
| 6,579,721 B1 * | 6/2003 | Natan et al. | ............... 436/164 |

FOREIGN PATENT DOCUMENTS

DE WO 01/51655 1/2001

OTHER PUBLICATIONS

International Search Report.
E. Stenberg et al., "Quantitative Determination of Surface Concentration of Protein with Surface Plasmon Resonance Using Radiolabeled Proteins," Jour. Colloidal and Inter. Sci., 1991, vol 43:2, pp. 513-526.
J. Homola et al., "Surface Plasmon Resonance Sensors: Review," Sensors and Actuators, 1999, vol. B 54, pp. 3-15.
S. Lofas et al., "A Novel Hydrogel Matrix on Gold Surfaces in Surface Plasmon Resonance Sensors for Fast and Efficient Covalent Immobilization of Ligands," J. Chem. Soc. Chem. Comm., 1990, pp. 1526-1528.
J. Spinke et al., "Molecular Recognition at Self-Assembled Monolayers: The Construction of Multicomponent Multilayers," Langmuir, 1993, vol. 9, pp. 1821-1825.
P. Englebienne, "Use of Colloidal Gold Surface Plasmon Resonance Peak Shirt to Infer Affinity Constants from the Interactions Between Protein Antigens and Antibodies Specific for Single or Multiple Epitopes," Analyst, 1998, vol. 123, pp. 1599-1603.
D. Eck et al., "Plasmon Resonance Measurements of the Adsorption and Adsorption Kinetics of a Biopolymer onto Gold Nanocolloids," Langmuir, 2001, vol. 17, pp. 957-960.
R. Elghanian et al., "Selective Colorimetric Detection of Polynucleotides Based on the Distance-Dependent Optical Properties of Gold Nanoparticles," Science, 1997, vol. 277, pp. 1078-1081.

(Continued)

*Primary Examiner*—Christopher L. Chin
(74) *Attorney, Agent, or Firm*—Fleshner & Kim, LLP

(57) ABSTRACT

Disclosed are sensors for use in testing biological, biochemical, chemical or environmental samples, and methods of making and using the same.

22 Claims, 5 Drawing Sheets

Detection Protocol

Biomolecular binding event on sensor chip detected by abscorbance change

OTHER PUBLICATIONS

J.J. Storhoff et al., "One-Pot Colorimetric Differentiation of Polynucleotides with Single Base Imperfections Using Gold Nanoparticle Probes," J. AM. Chem. Soc., 1998, vol. 120, pp. 1959-1964.

* cited by examiner

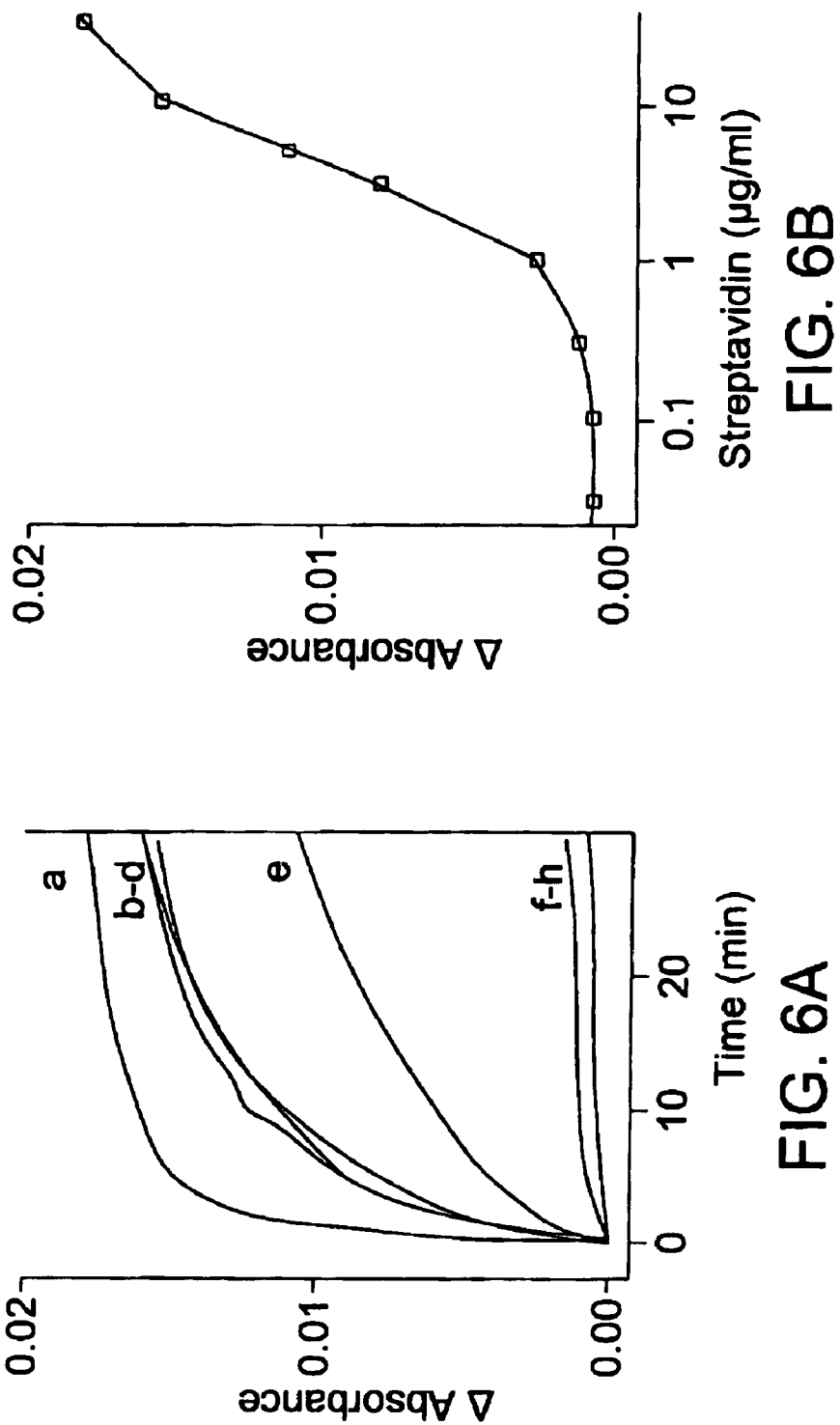

SENSOR FOR USE IN TESTING BIOLOGICAL, BIOCHEMICAL, CHEMICAL OR ENVIRONMENTAL SAMPLES

This application claims priority to Provisional Application Ser. No. 60/338,688, filed Dec. 11, 2001

This invention was made with Government support under Grant Nos. BES-97-33009 and BES-99-86477 awarded by the National Science Foundation. The United States Government has certain rights in the invention.

BACKGROUND OF THE INVENTION

1. Field of the Invention

The present invention relates to sensors for use in testing biological, biochemical, chemical or environmental samples, and methods of making and using the same.

2. Background of the Related Art

Analyses of biological, biochemical, chemical and environmental samples are invaluable, routinely used tools in health-related fields such as immunology, pharmacology, gene therapy, combinatorial chemistry, and the like. For example, in order to successfully implement therapeutic control of a biological process, it is imperative that a complete understanding of the binding between the species is obtained.

Many biochemical and biological analytical methods involve immobilization of a biological binding partner of a particular biological molecule on a surface, exposure of the surface and immobilized binding partner to a medium suspected of containing the biological molecule, and determination of the existence or extent of binding of the molecule to the surface-immobilized binding partner.

One such technique recently introduced involves surface plasmon resonance (SPR). Conventional SPR involves the use of a substrate, such as a glass slide, on one side of which is a thin metal film, a prism, a source of monochromatic and polarized light, a photodetector array and an analyte channel that directs a medium suspected of containing a particular analyte to the exposed surface of the metal film on the substrate. A face of the prism is separated from the second side of the substrate (i.e., the side opposite the metal film) by a thin film of refractive index matching fluid. Light from the light source is directed through the prism at an angle at which total internal reflection of the light results at the face of the prism. An evanescent field is generated as a result of this reflection, which extends from the prism into the metal film. This evanescent field can couple to an electromagnetic surface wave (a surface plasmon) at the metal film, causing surface plasmon resonance.

In such a device, coupling is achieved at a specific angle of incidence of the light with respect to the metal film (the SPR angle), at which the reflected light intensity goes through a minimum due to the resonance. This angle is determined by a photodetector array as the angle of reflectance and is highly sensitive to changes in the refractive index of a thin layer immediately adjacent to the surface of the metal film. Thus it is highly sensitive to coupling of an analyte to the metal film. For example, when a protein layer is adsorbed onto the metal surface from an analyte-containing medium delivered to the surface by the analyte channel, the SPR angle shifts to larger values and this shift is measured by the photodetector array. See, e.g., Stenberg et al., "Quantitative determination of surface concentration of protein with surface plasmon resonance using radiolabelled proteins," *Journal of Colloid and Interface Science,* 43:2, 513–526 (1991); Homola et al., "Surface plasmon resonance sensors: review," *Sensors and Actuators,* B 54, 3–15 (1999) and references cited therein. The instrumentation for analysis of biological samples using SPR is commercially available, for example, under the trade name BIAcore from Pharmacia Biosensor, Piscataway, N.J.

Although the introduction of SPR represented an extremely valuable contribution to the scientific community, current state-of-the-art commercial SPR instrumentation lacks the sensitivity needed to detect and analyze certain biological and chemical interactions that are at the vanguard of scientific research. Moreover, several complications have been observed with prior sensors for use in SPR which hinder the sensitivity of the technique.

For example, according to one technique for immobilizing a binding partner of an analyte on a surface plasmon resonance sensor, long chain hydroxy alkyl thiols are adsorbed onto a gold surface as a monolayer. The monolayer's exposed hydroxy groups are then activated with epichlorohydrin under basic conditions to form epoxides, which are then used to covalently attach a carboxylated dextran gel layer. A proteinaceous binding partner is then electrostatically adsorbed onto the dextran gel layer and subsequently covalently attached thereto. See, e.g., Lofas et al., "A novel matrix on gold surfaces in surface plasmon resonance sensors for fast and efficient covalent immobilization of ligands," *J. Chem Soc., Chem. Comm.,* 1526–1528 (1990).

The effectiveness of this approach, however, is limited by several factors. First, covalent attachment of the proteinaceous binding partner to the dextran gel can affect the binding partners activity, or even viability. Second, covalent attachment of the binding partner to the gel generally cannot be effected with control over the orientation of the binding partner with respect to the surface of the sensor (and, more importantly, with respect to the analyte-containing medium to be tested). Third, non-specific interactions at the dextran gel are promoted by the negative charge that it carries.

According to another technique, a mixed monolayer of hydroxyl and biotin-terminated alkyl thiols is prepared on a gold surface and streptavidin is bound to the surface-bound biotin. Biotin-labeled proteins, which are the binding partners of the desired analytes, are then attached to the empty sites on the streptavidin. See, e.g., Spinke et al., "Molecular recognition at self-assembled monolayers: the construction of multicomponent multilayers," *Langmuir,* 9, 1821–1825 (1993).

Because biotin must be covalently attached to the binding partner protein, however, this approach lacks control over orientation of the binding partner with respect to the analyte medium. Moreover, inactivation of the proteinaceous binding partner may also occur due to the formation of a covalent linkage.

Finally, as a practical limitation on its usefulness, conventional SPR reflectometry is difficult to realize in a large-scale array format because of the optics associated with the detection system. This is quite significant in view of the need for high-throughput biochemical assays based on protein arrays, such as those needed to measure the protein-protein and protein-ligand interactions for the many thousands of proteins identified by the human genome project as well as for DNA—DNA interactions in genomics.

One alternative to the use of conventional SPR methods involve colloidal surface plasmon resonance. Colloidal SPR is responsible for the intense colors exhibited by colloidal solutions of noble metals and is attributed to the collective oscillations of surface electrons induced by visible light.

Colloidal SPR is an interfacial phenomenon, and can be used in two complementary modes to transduce binding events at the colloid surface.

In one mode, the optical signal arises from the dependence of the peak intensity and position of the surface plasmon absorbance of gold nanoparticles upon the local refractive index of the surrounding medium, which is altered due to binding at the colloid-solution interface. This mode, which is analogous to conventional SPR, has been previously utilized to determine biomolecular binding on the surface of a colloid in suspension. See, e.g., Englebienne, "Use of colloidal gold surface plasmon resonance peak shifts to infer affinity constants from the interactions between protein antigens and antibodies specific for single or multiple epitopes," *Analyst*, 123, 1599–1603 (1998); Eck et al., "Plasmon resonance measurements of the absorption and adsorption kinetics of a biopolymer onto gold nanocolloids," *Langmuir*, 17, 957–960 (2001).

In the second mode, changes in the proximity of colloids due to their aggregation in suspension causes a large change in the absorbance spectrum of the colloidal suspension due to long-range coupling of surface plasmons. The interparticle distance-dependent color change of colloidal gold due to aggregation of gold colloids has been used in solution-based immunoassays and has more recently been employed to design a sensor capable of determining single base pair mismatches in DNA hybridization. See, e.g., Elghanian et al., "Selective colorimetric detection of polynucleotides based on the distance-dependent optical properties of gold nanoparticles," *Science*, 277, 1078–1081 (1997); Storhoff et al., "One-pot colorimetric differentiation of polynucleotides with single base imperfections using gold nanoparticles probes," *J. AM. Chem. Soc.*, 120, 1959–1964 (1998); and PCT International Publication Number WO 01/51655.

Neither of these modes, however, is sufficient to remedy the disadvantages of conventional SPR methods. For example, much like conventional SPR, neither of these modes can be employed in a large-scale array format on a solid surface. Accordingly, there remains a need for a simple, SPR chip-based sensor for analyzing biological, biochemical, chemical and environmental samples.

The above references are incorporated by reference herein where appropriate for appropriate teachings of additional or alternative details, features and/or technical background.

SUMMARY OF THE INVENTION

An object of the invention is to solve at least the above problems and/or disadvantages and to provide at least the advantages described hereinafter.

Accordingly, a first preferred embodiment of the present invention is directed to a sensor for use in testing biological, biochemical, chemical or environmental samples, said sensor comprising: (a) an optically transparent substrate having a first surface and a second surface; (b) optionally, a layer of a first functionalized material disposed over at least a portion of said first surface of said substrate; (c) a monolayer or sub-monolayer of a metallic material disposed over at least a portion of said first surface of said substrate or, when present, said layer of a first functionalized material, said monolayer being optically transparent and exhibiting colloidal surface plasmon resonance; (d) optionally, a layer of a second functionalized material disposed over at least a portion of said monolayer or sub-monolayer of metallic material; and (e) a reactive substance disposed over at least a portion of said monolayer or sub-monolayer of a metallic material or, when present, said layer of a second functionalized material, wherein said reactive substance interacts with a predetermined substance present in said biological, biochemical, chemical or environmental sample.

A second preferred embodiment of the present invention is directed to an array comprising a plurality of the sensors of the present invention.

A third preferred embodiment of the present invention is directed to a method of detecting the presence and/or quantifying the amount of a substance in a biological, biochemical, chemical or environmental sample which comprises the steps of: (i) measuring the absorbance of UV, visible, or infrared light by at least one sensor of the present invention; (ii) contacting a biological, biochemical, chemical or environmental sample with the sensor; and (iii) measuring the absorbance of UV, visible, or infrared light of the sensor following contact with the biological, biochemical, chemical or environmental sample; and (iv) determining the difference in absorbance of UV, visible, or infrared light of the sensor before and after contacting the biological, biochemical, chemical or environmental sample.

Additional advantages, objects, and features of the invention will be set forth in part in the description which follows and in part will become apparent to those having ordinary skill in the art upon examination of the following or may be learned from practice of the invention. The objects and advantages of the invention may be realized and attained as particularly pointed out in the appended claims.

BRIEF DESCRIPTION OF THE DRAWINGS

As shown in FIG. 5A, a slight negative baseline drift was observed, but this was extremely reproducible as shown by the overlaid plots for two different sensors. As shown in FIG. 5B, incubation of the $Au_{CM}$-MPA-biotin surface with a 10 µg/ml solution of streptavidin or 50 µg/ml antibiotin mAb resulted in a dramatic, time-dependent increase in absorbance. As shown in FIG. 5C, incubation of the biotin-mAb complex in an aqueous solution of 1 mM biotin resulted in a decrease in absorbance as a function of time, due to dissociation of the mAb from the surface.

FIGS. 6A–6B show the measurement of concentration-dependent absorbance changes to determine the dynamic range and sensitivity of a sensor of the present invention. FIG. 6A shows representative plots of the sensor response as a function of time for different streptavidin concentrations. As shown in FIG. 6B, a calibration plot of the absorbance change at 550 nm, after 30 minutes incubation, versus streptavidin concentration yielded a detection limit of 1 µg/ml streptavidin (16.6 nM streptavidin tetramer).

DETAILED DESCRIPTION OF PREFERRED EMBODIMENTS

Figure 1:
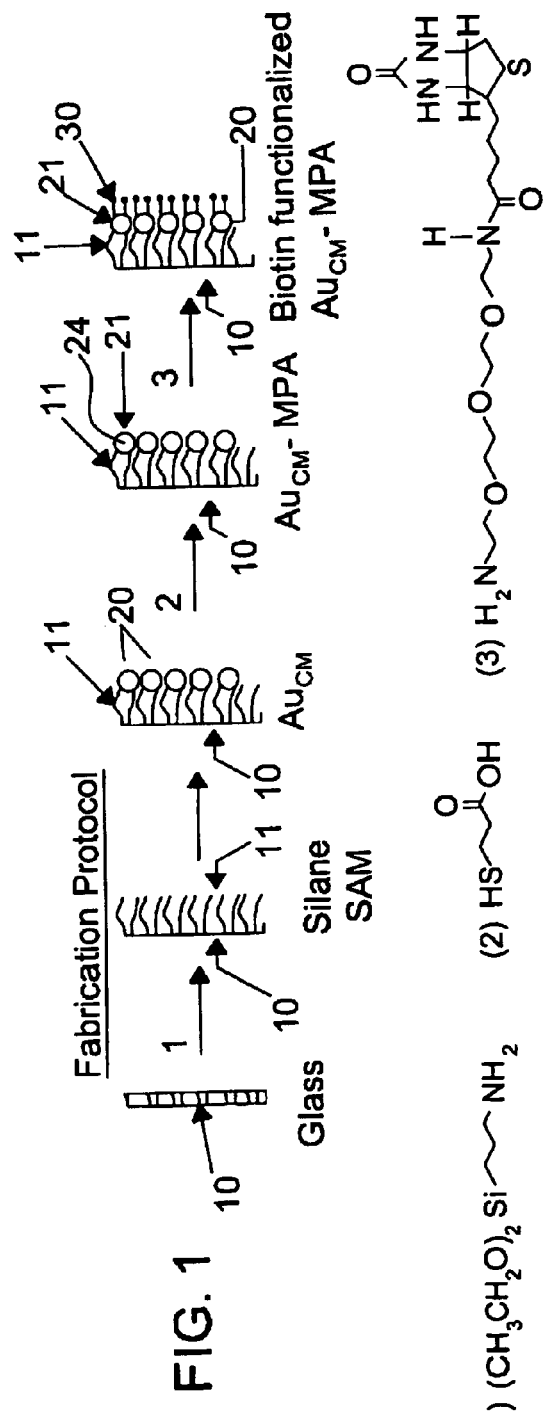
FIG. 1 is a graphic depiction of a preferred fabrication protocol for a particularly preferred sensor of the present invention.

A first preferred embodiment of the present invention is directed to a sensor for use in testing biological, biochemical, chemical or environmental samples which comprises: (i) an optically transparent substrate having a first surface and a second surface; (ii) a monolayer or sub-monolayer of a metallic material disposed over at least a portion of the first surface of the substrate, the monolayer or sub-monolayer of metallic material being optically transparent and capable of exhibiting colloidal surface plasmon resonance; and (iii) a reactive substance disposed over at least a portion of the monolayer or sub-monolayer of metallic material.

The substrate may be comprised of any suitable material known to those skilled in the art, provided that it is optically transparent. As used herein, the term "optically transparent" is intended to mean a substance that permits transmission of light in the ultraviolet region (about 200 to about 500 nm), visible region (about 500 to about 800 nm), or infrared (greater than about 800 nm) of the spectrum.

Illustrative examples of suitable materials for use as the optically transparent substrate (10) include, but are not limited to, the following: glass; quartz; organic films, such as polycarbonates, polyolefins and acrylic and methacrylic resins; inorganic materials, such as germanium, galium arsenide, silicon-derived materials (e.g. fused silica, silicone gels and polysiloxanes) and tin-derived materials (e.g. tin oxide and indium-doped tin oxide (ITO)); and the like. A particularly preferred material for use as the optically transparent substrate is glass.

A monolayer or sub-monolayer of metallic material is disposed over at least a portion of one surface of the optically transparent substrate. The monolayer or sub-monolayer of metallic material (20) preferably comprises a plurality of nanoparticles of a metallic material on one surface of the optically transparent substrate According to certain particularly preferred embodiments of the present invention, the monolayer or sub-monolayer of a metallic material is preferably comprised of gold or silver nanoparticles or any other material that exhibits colloidal SPR behavior, including metal/inorganic nanoshells.

According to one embodiment of the present invention, a sub-monolayer of a metallic material is employed in the inventive sensor. As used herein, the term "sub-monolayer" is intended to mean an assembly of particles chemisorbed on a surface, in which the particles are oriented roughly perpendicular to the surface, but which is less than a complete monolayer of the particles on the surface.

According to an alternative embodiment of the present invention, the monolayer of a metallic material may also be a self-assembled monolayer. As used herein, the term "self-assembled monolayer" is intended to mean a relatively ordered assembly of particles spontaneously chemisorbed on a surface, in which the particles are oriented approximately parallel to each other and roughly perpendicular to the surface.

Any suitable metallic material known to those skilled in the art may be employed as the monolayer or sub-monolayer of a metallic material. Suitable metallic materials are those which exhibit colloidal surface plasmon resonance and which can form an optically transparent monolayer. Particularly preferred metallic materials are those which can form an optically transparent self-assembled monolayer. Illustrative examples of suitable metals for forming the monolayer of metallic material include, but are not limited to, silver, gold, copper, aluminum, platinum, titanium, and indium and combinations derived from these materials.

According to certain preferred embodiments of the present invention, the metallic material employed in the various embodiments of the present invention is a noble metal, such as gold or silver, or mixtures thereof, such as Au/Ag. Preferably, the metallic material is gold or a mixture thereof, and more preferably the metallic metal is gold. According to a particularly preferred embodiment of the present invention, the metallic material is silver encapsulated within a shell of gold.

When the monolayer or sub-monolayer of metallic material is composed of a plurality of nanoparticles on the surface of the optically transparent substrate, those particles are preferably of a size in the range of 5–150 nm and are spaced such that the metallic material exhibits an appropriate surface plasmon absorbance spectrum. Preferably, when the monolayer or sub-monolayer is composed of colloidal gold, the size of the nanoparticles is generally less than about 120 nm.

According to certain preferred embodiments of the present invention, the size of the nanoparticles of metallic material is preferably about 10–100 nm, more preferably about 40–80 nm and most preferably about 60 nm.

According to an alternative embodiment of the present invention, the size of the nanoparticles of metallic material is less than about 50 nm, preferably less than about 40 nm, and more preferably less than about 20 nm, such as in the range of 10–15 nm (e.g. 13.4±0.9 nm). According to such an alternative embodiment, the colloidal gold nanoparticles are preferably spaced edge-to-edge less than about 30 nm apart, more preferably less than about 20 nm apart, and most preferably about 15 nm apart (e.g. a center-to-center distance of about 28.1 nm for particles about 13.4±0.9 nm in size)

A reactive substance is disposed over at least a portion of the monolayer or sub-monolayer of a metallic material. This reactive substance interacts with a predetermined substance present in the biological, biochemical, chemical or environmental solution being tested with the sensor of the present invention. Any suitable reactive substance may be employed in the present invention, provided that it does not deleteriously affect either the metallic material or the optically transparent substrate.

According to certain preferred embodiments of the present invention, the reactive substance is an agent involved in biological binding with at least one predetermined substance present in the biological, biochemical, chemical or environmental sample being tested. As used herein, the term "biological binding" is intended to mean the interaction between a corresponding pair of molecules that exhibit mutually affinity or binding capacity, typically specific or non-specific binding or interaction, including biochemical, physiological and/or pharmaceutical interactions, such as pairs of proteins, nucleic acids, glycoproteins, carbohydrates, hormones and the like. Illustrative examples of such corresponding pairs or molecules include, but are not limited to, the following: antibody/antigen; antibody/hapten; enzyme/substrate; enzyme/cofactor; enzyme/inhibitor; binding protein/substrate; carrier protein/substrate; lectin/carbohydrate; receptor/hormone; receptor/effector; nucleic acid strand/complementary nucleic acid strand; protein/nucleic acid repressor or inducer; ligand/cell surface receptor; and virus/ligand.

According to a particularly preferred embodiment of the present invention, a layer of a first functionalized material is disposed over at least a portion of the first surface of the optically active substrate. As used herein, the term "functionalized material" is intended to mean a chemical compound having at least one, and preferably more than one, functional group that interacts with a moiety on the optically transparent substrate and/or the monolayer or sub-monolayer of metallic material.

In such an embodiment of the present invention, the monolayer or sub-monolayer of metallic material is disposed over at least a portion of the layer of the first functionalized material. The first functionalized material preferably improves the adherence of the monolayer or sub-monolayer of metallic material to the optically transparent substrate. Accordingly, any material which is optically transparent and adheres to both the optically transparent substrate and the monolayer or sub-monolayer of metallic material, but is not deleterious to either, may be employed as the first functionalized material.

Suitable compounds for use as the first functionalized material are known to those skilled in the art and include, for example, organosilanes, particularly hydrolyzed mono-, di- and trialkoxysilanes containing the functional groups CN, $NH_2$, 2-pyridyl, $P(C_6H_5)_2$ and/or SH, and carboxyl-terminated organothiols. A particularly preferred example of a first functionalized material (11) is gamma-aminopropyltriethoxysilane.

The choice of a particular first functionalized material to be employed in such an embodiment of the present invention will therefore depend, at least in part, upon the specific optically transparent substrate and particular metallic material employed. Accordingly, the choice of a particular first functionalized material may be determined empirically by one skilled in the art, in view of the particular metallic material and optically transparent substrate being used.

According to another particularly preferred embodiment of the present invention, a layer of a second functionalized material is disposed over at least a portion of the monolayer or sub-monolayer of metallic material. In such an embodiment of the present invention, the reactive substance is disposed over at least a portion of the layer of the second functionalized material.

The second functionalized material preferably improves the adherence of the reactive substance to the monolayer or sub-monolayer of metallic material. Accordingly, any material which adheres to both the metallic material and the reactive substance, but is not deleterious to either, may be employed as the second functionalized material. Suitable compounds for use as the second functionalized material are known to those skilled in the art and include, for example, organic compounds containing one or more of the functional groups COOH, CN, $NH_2$, 2-pyridyl, $P(C_6H_5)_2$ and/or SH. Particularly preferred examples of a second functionalized material are carboxyl-terminated organothiols, such as 3-mercaptopropionic acid.

The choice of a particular second functionalized material to be employed in such an embodiment of the present invention will therefore depend, at least in part, upon the particular metallic material and specific reactive substance employed. Accordingly, the choice of a particular second functionalized material may be determined empirically by one skilled in the art, in view of the particular metallic material and reactive substance being used.

The sensor(s) of the present invention are preferably employed in combination with a means for detection of transmitted light in the ultraviolet region (about 200 to about 500 nm), visible region (about 500 to about 800 nm) and/or infrared region (greater than about 800 nm) of the spectrum. Commercially available examples of such means for detection of transmitted light include, but are not limited to, UV-vis spectrophotometers, infrared spectrometers and flatbed optical scanners.

A second preferred embodiment of the present invention is directed to a plurality of the sensors of the first or second preferred embodiments above are arranged in an array format. According to such an embodiment, an array of sensors is preferably employed in combination with a means for detection of transmitted light in the ultraviolet region (about 200 to about 500 nm) and/or visible region (about 500 to about 800 nm), such as a flatbed optical scanner or CCD camera, or the infrared region of the spectrum (greater than about 800 nm). Such an embodiment of the present invention is particularly useful for use in an endpoint-assay or as a screening tool in combinatorial chemistry, proteomics and/or genomics.

The sensors of the present invention may be preferably prepared using chemisorption or the solution self-assembly of metal colloids, such as gold colloids, on a surface, where the assembly is stabilized by strong attractive colloid-surface interactions and laterally by repulsive colloid-colloid electrostatic interactions. More preferably, the sensors of the present invention are prepared from a monolayer of gold colloids formed by incubation from solution on a functionalized glass slide. Most preferably, the sensors of the present invention are preferably fabricated by solution self-assembly of a series of monolayers.

Referring now to FIG. 1, the optically transparent substrate (10), such as a glass slide, is first functionalized by the formation of a self-assembled monolayer (SAM) of a first functionalized material (11), such as gamma-aminopropyltriethoxysilane, to present a SAM on the substrate surface which has a pendant functional group, such as an amine.

Next, the substrate surface having a SAM of a first functionalized material is immersed in a solution of colloidal metallic material, such as gold, to form a self-assembled or chemisorbed monolayer or sub-monolayer of colloids of metallic material (20) on the SAM of the first functionalized material (11). Preferably, the binding of the colloids of metallic material to the SAM of the first functionalized material is sufficiently strong to withstand further chemical modification of the colloids of metallic material without causing the detachment of the monolayer or sub-monlayer of the metallic material (20) from the SAM of the first functionalized material (11).

Suitable colloids of metallic material may be prepared by any of the methods known to those skilled in the art. For example, when the metallic metal is gold, gold colloids may be prepared by trisodium citrate reduction of gold tetrachloroaurate. See, e.g., Grabar et al., "Preparation and characterization of Au colloid monolayers," *Anal. Chem.*, 67, 735–743 (1995). This is a simple, one-step reduction that can be controlled to provide monodisperse gold nanoparticles of a predetermined size in the range of 5–120 nm.

Following preparation of the SAM of metallic material (20) on the SAM of the first functionalized material (11), a reactive material (30) is deposited on the monolayer or sub-monolayer of the metallic material (20). Preferably, the reactive material (30) is deposited on the monolayer or sub-monolayer of the metallic material (20) by immersing the modified substrate in a suitable solution of the reactive material.

Alternatively, a self-assembled monolayer of a second functionalized material (21), such as 3-mercaptopropionic acid, is formed on the monolayer or sub-monolayer of metallic material (20) prior to deposition of the reaction material (30). A SAM of a second functionalized material is prepared by incubating the substrate (10) having a SAM of a first functionalized material (11) and a monolayer or sub-monolayer of a metallic material (20) in a solution of the second functionalized material so as to form a SAM of the second functionalized material (21). Preferably, the binding of the SAM of the second functionalized material (21) to the monolayer or sub-monolayer of the metallic material (20) is sufficiently strong to withstand further chemical modification of the second functionalized material without causing the detachment of the SAM of the second functionalized material from the monolayer or sub-monolayer of metallic material.

Following preparation of the SAM of the second functionalized material on the monolayer or sub-monolayer of metallic material, a reactive material (30) is deposited on the monolayer of the second functionalized material (21). Preferably, the reactive material (30) is deposited on the SAM of the second functionalized material (21) by immersing the modified substrate in a suitable solution of the reactive material.

Moreover, the second functionalized material may optionally be chemically modified prior to deposition of the reactive material thereon. For example, when the second functionalized material is 3-mercpatopropionic acid, the terminal carboxyl group may be activated with 1-ethyl-3-(dimethylamino)propyl carbodiimide (EDAC) and pentafluorophenol to facilitate the binding of certain reactive substances, such as biotin and its derivatives (e.g. (+)-biotinyl-3,6,9-trioxaundecanediamine), to the SAM of the second functionalized material.

Figure 2:
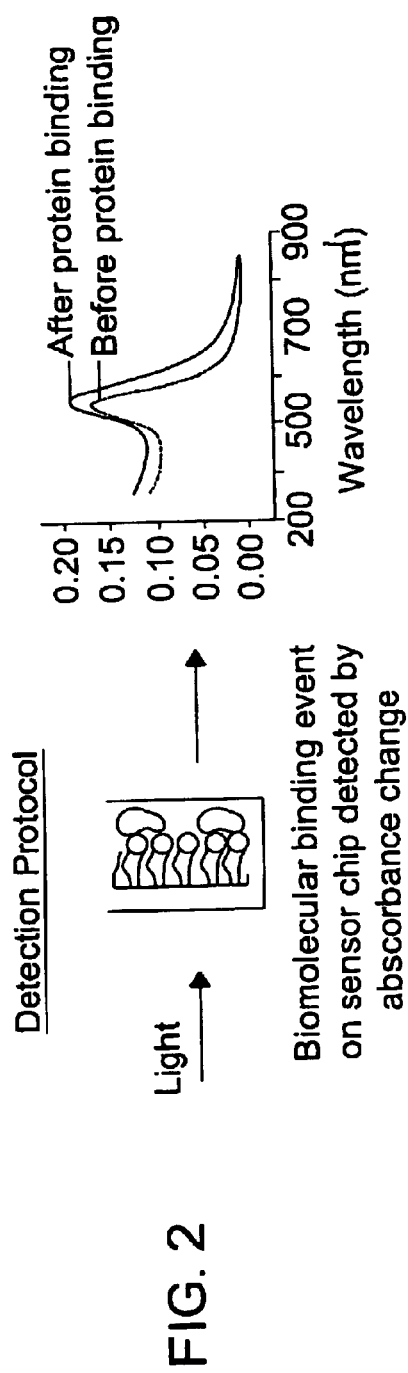
FIG. 2 is a graphic depiction of a preferred detection protocol using a preferred sensor of the present invention.

Another preferred embodiment of the present invention is directed to a method of detecting the presence and/or quantifying the amount of a substance in a biological, biochemical, chemical or environmental sample. Referring now to FIG. 2, the transmission of light through at least one sensor of the present invention is first measured and the sensor is then exposed to a biological, biochemical, chemical or environmental sample. Binding of a substance in the sample to the reactive substance (30) on the sensor causes a change on the local refractive index surrounding the metallic material (20), which is observed as a change in the surface plasmon absorption spectrum of the metallic material (as measured by the transmission of light through the sensor).

The change in the surface plasmon absorption spectrum of the metallic material may be measured by any suitable means for detection of transmitted light. Suitable means include UV-vis spectrophotometers, such as those available commercially from companies such as Beckman Coulter (DU Series 500 Scanning Spectrophotometers and DU Series 600 High Performance Spectrophotometers), Spectral Instruments (400 Series spectrometers), Varian Instruments (Cary 300Bio spectrophotometer), Safas Monaco (UVmc series spectrophotometers and D.E.S. spectrophotometers), Hitachi Instruments (U3010/3310 spectrophotometers) and others. Other means for detection of transmitted light include CCD cameras and flatbed optical scanners, which are also commercially available, such as a UMAX super vista S-12 flatbed scanner (UMAX Technologies, Inc.), preferably in combination with means for converting the image to grey scale and/or means for determining the density of an image, such as Scion Image software (Scion Corp.

EXAMPLES

Synthesis and Characterization of gold colloids. All glassware used for preparation of colloids was thoroughly washed with aqua regia (3:1 $HNO_3$:HCl), rinsed extensively with distilled water and then dried in an oven at 100° C. for 2 hr. Gold colloids were prepared by sodium citrate reduction of $HAuCl_4 \cdot 3H_2O$ (see Grabar et al., Anal. Chem. 67, 735–743 (1995)). 250 ml of 1 mM $HAuCl_4$ (Aldrich) was brought to a vigorous boil with stirring in a round bottom flask fitted with a reflux condenser and 25 ml of 38.8 mM sodium citrate was rapidly added to the solution. The solution was boiled for another 15 min, during which time the solution changed color from pale yellow to deep red. The solution was allowed to cool to room temperature with continued stirring. The suspension was filtered using a 0.22 μm filter (Corning, N.Y.) and stored at 4° C. till further use.

The diameter of the colloids was determined by transmission electron microscopy (TEM). A small drop of the colloidal gold suspension was placed on a lysine-coated formvar grid, and excess solution was wicked away by a filter paper. The grid was subsequently dried in air and imaged on a Philips 400S transmission electron microscope. The accelerating voltage was 80 kV. The size of the gold colloids was determined by image analysis of TEM images of gold colloids (n=150).

Fabrication and characterization of colloidal gold monolayer on glass ($Au_{CM}$). Glass coverslips (VWR Scientific) cut into 10×50 mm pieces were used as the substrate for assembly of a colloidal gold monolayer. The glass coverslips were cleaned by sonication for 5 minutes in hot RBS 35 detergent (Pierce), and then washed extensively with distilled water. The substrates were further cleaned in a 1:1 solution of methanol and concentrated HCl for 30 min., washed extensively with distilled water and dried overnight at 60° C. The cleaned glass substrates were immersed in a 10% (v/v) solution of gamma-aminopropyltriethoxysilane (APTES) in anhydrous ethanol for 15 min., rinsed five times in ethanol with sonication, and dried at 120° C. for 3 h. The silanized glass coverslips were subsequently immersed overnight in a colloidal gold solution (11.6 nM) to form a self-assembled monolayer of the gold colloids on glass ($Au_{CM}$). The immobilized colloids were imaged by AFM in contact mode in air using standard $Si_3N_4$ cantilevers on a Multimode Nanoscope IIIa (Digital Instruments, Inc.)

Functionalization of $Au_{CM}$. $Au_{CM}$ was modified by the formation of a SAM of mecaptopropionic acid (MPA) by incubation of the colloid monolayer on glass in a 1 mM solution of MPA in absolute ethanol for 10 min at room temperature (termed $Au_{CM}$-MPA). These samples were used for fibrinogen adsorption studies. $Au_{CM}$-MPA samples were functionalized with biotin as follows: $Au_{CM}$-MPA samples were immersed in an ethanol solution 0.1 M 1-ethyl-3-(dimethylamino)propyl carbodiimide (EDAC, Sigma) and 0.2 M pentafluorphenol (PFP, Sigma) for 20 min at room temperature, rinsed thrice with ethanol and then immersed in a 100 μg/ml ethanol solution of (+)-biotinyl-3,6,9-trioxaudecanediamine (EZ-Link-biotin-PEO-LC-amine, Pierce) for 2 h., washed with ethanol and stored in PBS at 4° C. until further use.

Absorbance measurements of immobilized gold colloids on glass. All the absorbance measurements were done on a temperature-controlled spectrophotometer (Cary 300Bio, Varian Instruments). A rectangular glass flow cell of 4 mm width was designed to hold the $Au_{CM}$ samples. Samples were positioned in the center of the glass cell using two teflon guides on top of the cell. Spectra were collected in transmission mode over 350–750 nm range. Glass substrates functionalized with colloidal gold were scanned using a commercial UMAX super vista S-12 flatbed scanner (UMAX Technologies, Inc.). For quantitative analysis, the color images were converted to gray scale and the mean gray scale density of each image was calculated using Scion Image software (Scion Corp.)

Figure 3A:
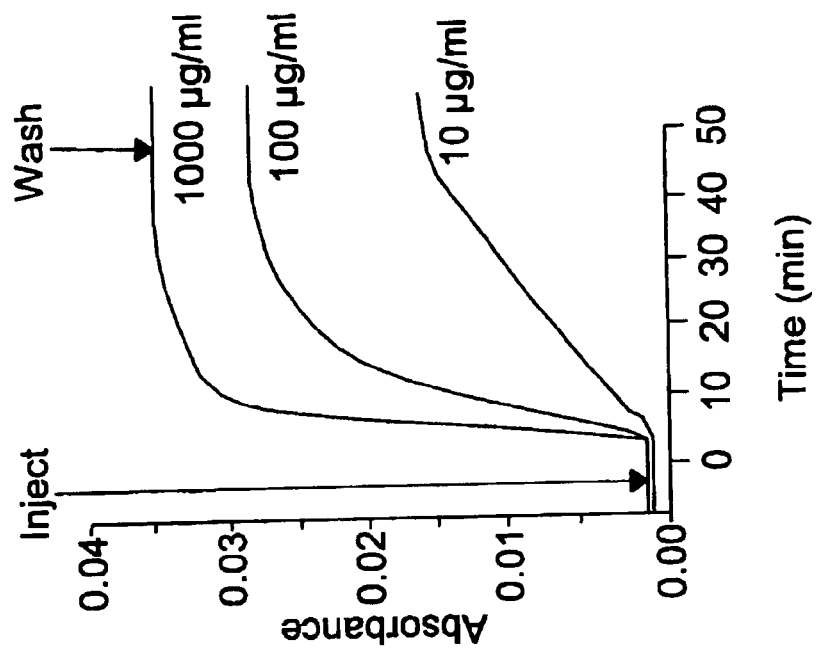
FIGS. 3A and 3B are graphs depicting the adsorption of fibrinogen to a sensor of the present invention.
Figure 3B:
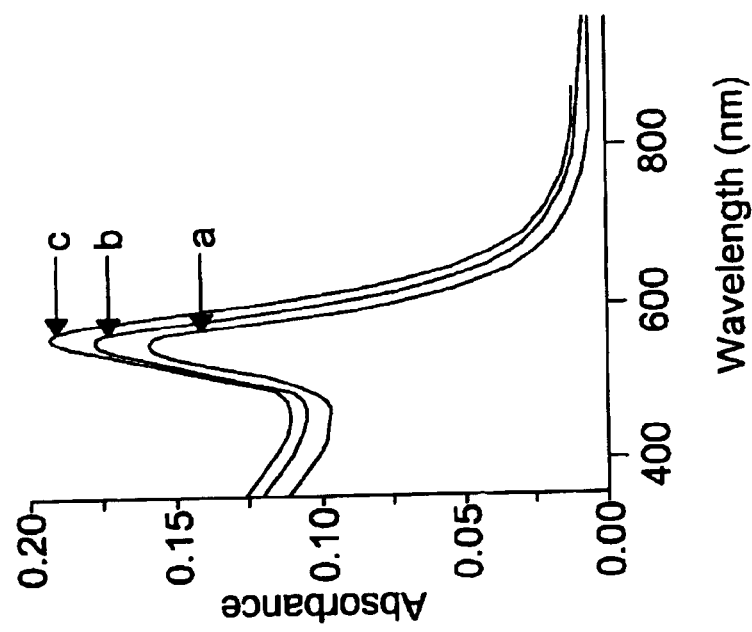

Referring now to FIG. 3, FIG. 3A is the spectrum of $Au_{CM}$-MPA before and after incubation with fibrinogen at two different solution concentrations for 2 hours at room temperature. A significant increase in the absorbance at 550 nm was observed, due to the increase in the local refractive index at the colloid-solution interface caused by the adsorption of fibrinogen. By monitoring the absorbance changes at 550 nm in real time, both the concentration and time-dependent adsorption of fibrinogen adsorption can be successfully measured, as shown in FIG. 3B. These results show that the kinetics of adsorption are directly related to the solution concentration of the protein and that the maximum amount of fibrinogen bound to the surface at steady state is directly related to the solution concentration, and can be attributed to different packing configurations of the protein on the surface.

Figure 4A:
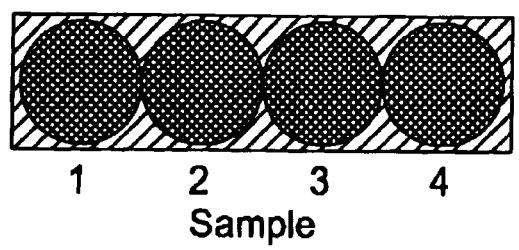
FIG. 4A shows scans prepared on a commercially available flatbed optical scanner of four substrates: (i) $Au_{CM}$; (ii) $Au_{CM}$-MPA; (iii) $Au_{CM}$-MPA incubated with a 10 µg/ml solution of fibrinogen for 30 min; and (iv) $Au_{CM}$-MPA incubated with a 1000 µg/ml solution of fibrinogen for 30 min. Conversion of these images to gray scale and calculation of the average intensity allows quantitative evaluation of the color differences, as shown in FIG. 4B.
Figure 4B:
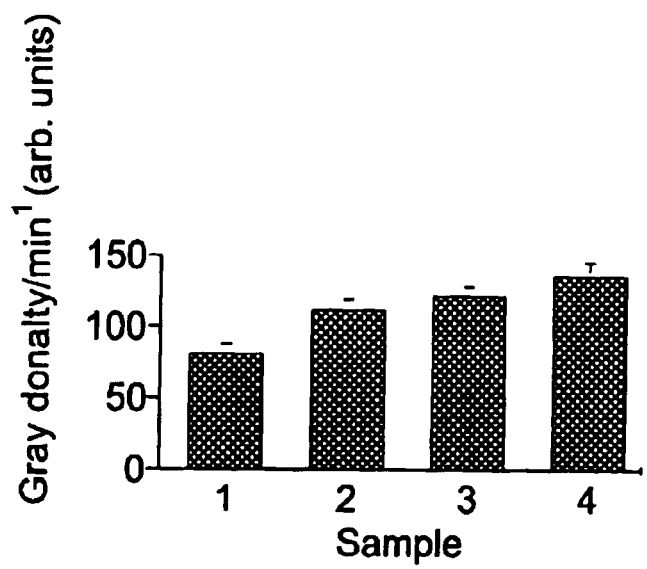

Referring now to FIG. 4, FIG. 4A shows scans prepared on a commercially available flatbed optical scanner of four substrates: (i) $Au_{CM}$; (ii) $Au_{CM}$-MPA; (iii) $Au_{CM}$-MPA incubated with a 10 μg/ml solution of fibrinogen for 30 min; and (iv) $Au_{CM}$-MPA incubated with a 1000 μg/ml solution of fibrinogen for 30 min. Conversion of these images to gray scale and calculation of the average intensity allows quantitative evaluation of the color differences, as shown in FIG. 4B. These results suggested that the sensors of the present invention may be employed in an array format for endpoint assays.

Referring now to FIG. 5, receptor-ligand binding studies were conducted using the model biotin-streptavidin and biotin-antibiotin monoclonal antibody (mAb) receptor-ligand pairs. The binding experiments were performed in batch mode, where biotin-functionalized surfaces were sequentially immersed in PBS-Tween20 buffer (to establish baseline), a solution of streptavidin or antibiotin mAb (to initiate binding) and a 1 mM solution of biotin (to initiate dissociation of the protein-ligand complex).

Figure 5C:
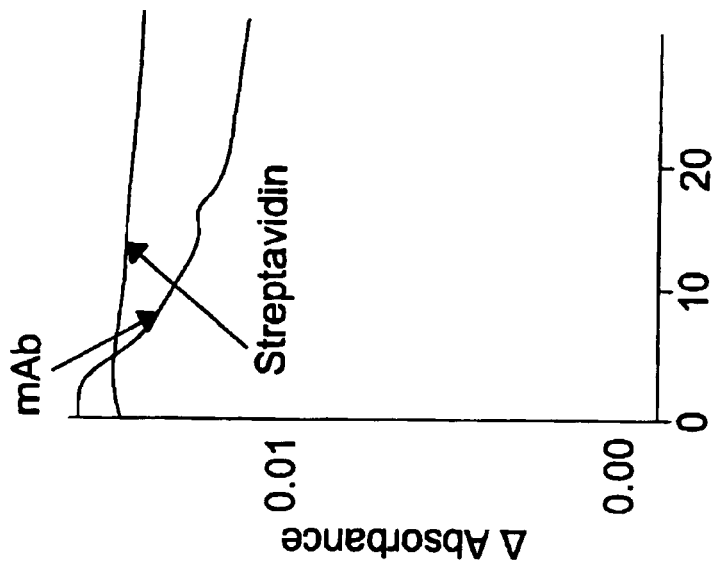
FIGS. 5A–5C shows the results of receptor-ligand binding studies conducted using the model biotin-streptavidin and biotin-antibiotin monoclonal antibody (mAb) receptor-ligand pairs.
Figure 5B:
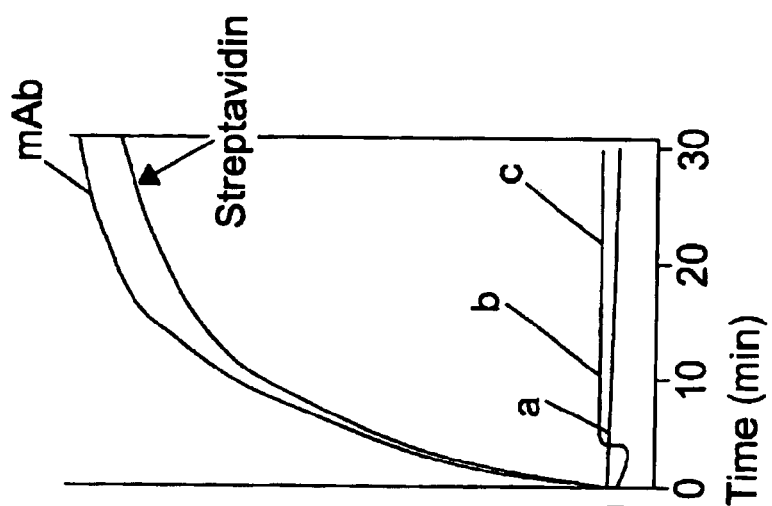
Figure 5A:
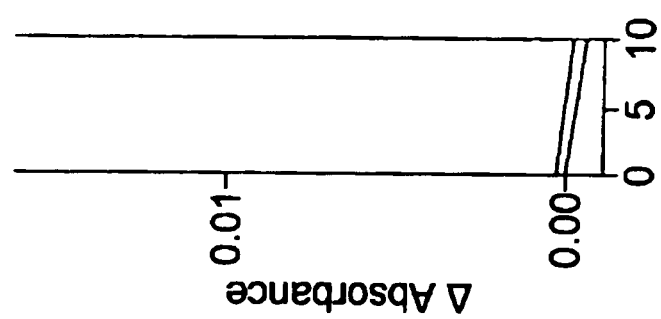

As shown in FIG. 5A, a slight negative baseline drift was observed, but this was extremely reproducible as shown by the overlaid plots for two different sensors.

As shown in FIG. 5B, incubation of the $Au_{CM}$-MPA-biotin surface with a 10 μg/ml solution of streptavidin or 50 μg/ml antibiotin mAb resulted in a dramatic, time-dependent increase in absorbance. In control experiments, incubation of the $Au_{CM}$-MPA-biotin surface with BSA, antihuman IgG or streptavidin whose biotin binding sites were blocked by pre-incubation with biotin did not result in any change in absorbance as shown in FIG. 5B.

As shown in FIG. 5C, incubation of the biotin-mAb complex in an aqueous solution of 1 mM biotin resulted in a decrease in absorbance as a function of time, due to dissociation of the mAb from the surface.

Concentration-dependent absorbance changes were measured to determine the dynamic range and sensitivity of a sensor of the present invention. An $Au_{CM}$-MPA-biotin sensor was incubate in streptavidin as a function of solution concentrations ranging from 0.03 μg/ml to 30 μg/ml, and the absorbance change at 550 nm was measured as a function of time. FIG. 6A shows representative plots of the sensor response as a function of time for different streptavidin concentrations. Both the kinetic and steady-state response of this sensor were highly reproducible, as shown for three different replicates at the same concentration of streptavidin (10 μg/ml) in FIG. 6A (plots b, c and d). As shown in FIG. 6B, a calibration plot of the absorbance change at 550 nm, after 30 minutes incubation, versus streptavidin concentration yielded a detection limit of 1 μg/ml streptavidin (16.6 nM streptavidin tetramer).

The foregoing embodiments and advantages are merely exemplary and are not to be construed as limiting the present invention. The present teaching can be readily applied to other types of apparatuses. The description of the present invention is intended to be illustrative, and not to limit the scope of the claims. Many alternatives, modifications, and variations will be apparent to those skilled in the art.

What is claimed is:

1. A method of detecting the presence and/or quantifying the amount of a substance in a biological, biochemical, chemical or environmental sample, which comprises the steps of:
   (i) measuring absorbance of uv, visible and/or infrared light by at least one sensor comprising:
      (a) an optically transparent substrate having a first surface and a second surface;
      (b) optionally, a layer of a first functionalized material disposed over at least a portion of said first surface of said substrate;
      (c) a monolayer or sub-monolayer of a metallic material disposed over at least a portion of said first surface of said substrate or, when present, said layer of a first functionalized material, said monolayer being optically transparent and exhibiting colloidal surface plasmon resonance;
      (d) optionally, a layer of a second functionalized material disposed over at least a portion of said monolayer or sub-monolayer of metallic material; and
      (e) a reactive substance disposed over at least a portion of said monolayer or sub-monolayer of a metallic material or, when present, said layer of a second functionalized material, wherein said reactive substance interacts with a predetermined substance present in said biological, biochemical, chemical or environmental sample;
   (ii) contacting a biological, biochemical, chemical or environmental sample with said sensor;
   (iii) measuring absorbance of uv infrared and/or visible light of said sensor following contact with said biological, biochemical, chemical or environmental sample; and
   (iv) determining the difference in absorbance of uv, visible and/or infrared light of said sensor before and after contacting said biological, biochemical, chemical or environmental sample, wherein a difference in absorbance indicates the presence and/or amount of said substance in, said biological, biochemical, chemical or environmental sample.

2. The method of claim 1, wherein said monolayer or sub-monolayer of metallic material is a monolayer of metallic material.

3. The method of claim 1, wherein said monolayer or sub-monolayer of metallic material is a sub-monolayer of metallic material.

4. The method of claim 2, wherein said monolayer of metallic material is a self-assembled monolayer of metallic material.

5. The method of claim 2, wherein said monolayer of metallic material is formed by chemisorption.

6. The method of any one of claims 2–5, wherein said monolayer or sub-monolayer of metallic material comprises a plurality of nanoparticles of metallic material.

7. The method of any one of claims 2–5, wherein said metallic material is a noble metal.

8. The method of any one of claims 2–5, wherein said metallic material is selected from the group consisting of gold, silver, indium, aluminum, copper, platinum, titanium, and mixtures of any two or more thereof.

9. The method of claim 6, wherein said nanoparticles of metallic material comprise layered core-shell particles.

10. The method of claim 9, wherein said core-shell particles comprise silver and gold.

11. The method of any one of claims 2–5, wherein said metallic material is gold.

12. The method of claim 6, wherein said nanoparticles are of a size in the range of about 10–100 nm.

13. The method of claim 6, wherein said nanoparticles are of a size in the range of about 40–80 nm.

14. The method of claim 6, wherein said nanoparticles are about 60 nm.

15. The method of claim 1, wherein said optically transparent substrate is selected from the group consisting of glass, quartz, organic films, germanium, galium arsenide, fused silica, silicone gels, polysiloxanes, tin oxide and indium-doped tin oxide.

16. The method of claim 1, wherein said reactive substance is a member of a pair selected from the group consisting of antibody/antigen; antibody/hapten; enzyme/substrate; enzyme/cofactor; enzyme/inhibitor; binding protein/substrate; carrier protein/substrate; lectin/carbohydrate; receptor/hormone; receptor/effector; nucleic acid strand/complementary nucleic acid strand; protein/nucleic acid repressor; protein/nucleic acid inducer; ligand/cell surface receptor; and virus/ligand.

17. The method of claim 1, wherein said first functionalized material is an organosilane or an organothiol.

18. The method of claim 1, wherein said first functionalized material is selected from the group consisting of hydrolyzed mono-, di- and trialkoxysilanes or mono-, di- and trichlorosilane which contain at least one CN, $NH_2$, 2-pyridyl, $P(C_6H_5)_2$ and/or SH group, and carboxyl-terminated organothiols.

19. The method of claim 18, wherein said first functionalized material is gama-aminopropyltriethoxysilane.

20. The method of claim 1, wherein said second functionalized material is an organic compound containing one or more of the functional groups COOH, CN, $NH_2$, 2-pyridyl, $P(C_6H_5)_2$ and/or SH.

21. The method of claim 20, wherein said second functionalized material is a carboxyl-terminated organothiol.

22. The method of claim 20, wherein said second functionalized material is 3-mercaptopropionic acid.

* * * * *